(12) United States Patent
Bakan et al.

(10) Patent No.: US 9,119,793 B1
(45) Date of Patent: Sep. 1, 2015

(54) GASTRORETENTIVE DOSAGE FORMS FOR DOXYCYCLINE

(75) Inventors: Douglas A. Bakan, San Diego, CA (US); Waranush Jitpraphai, Chandler, AZ (US); Steven B. Newhard, Scottsdale, AZ (US); Mitchell S. Wortzman, Scottsdale, AZ (US)

(73) Assignee: Medicis Pharmaceutical Corporation, Scottsdale, AZ (US)

( * ) Notice: Subject to any disclaimer, the term of this patent is extended or adjusted under 35 U.S.C. 154(b) by 0 days.

(21) Appl. No.: 13/536,052

(22) Filed: Jun. 28, 2012

Related U.S. Application Data

(60) Provisional application No. 61/501,888, filed on Jun. 28, 2011, provisional application No. 61/508,459, filed on Jul. 15, 2011, provisional application No. 61/508,468, filed on Jul. 15, 2011, provisional application No. 61/508,484, filed on Jul. 15, 2011, provisional application No. 61/508,158, filed on Jul. 15, 2011, provisional application No. 61/508,338, filed on Jul. 15, 2011.

(51) Int. Cl.
*A61K 35/14* (2015.01)
*A61K 9/24* (2006.01)

(52) U.S. Cl.
CPC ...................................... *A61K 9/209* (2013.01)

(58) Field of Classification Search
None
See application file for complete search history.

(56) References Cited

U.S. PATENT DOCUMENTS

| | | | |
|---|---|---|---|
| 4,952,402 A | 8/1990 | Sparks et al. |
| 5,000,886 A | 3/1991 | Lawter et al. |
| 5,051,262 A | 9/1991 | Panoz et al. |
| 5,122,519 A | 6/1992 | Ritter |
| 5,354,556 A | 10/1994 | Sparks et al. |
| 5,516,531 A | 5/1996 | Makino et al. |
| 5,538,954 A | 7/1996 | Koch et al. |
| 5,780,055 A | 7/1998 | Habib et al. |
| 5,789,395 A | 8/1998 | Amin et al. |
| 5,919,775 A | 7/1999 | Amin et al. |
| 6,077,533 A | 6/2000 | Oshlack et al. |
| 6,080,426 A | 6/2000 | Amey et al. |
| 6,193,994 B1 | 2/2001 | Lee et al. |
| 6,245,350 B1 | 6/2001 | Amey et al. |
| 6,340,475 B2 | 1/2002 | Shell et al. |
| 6,497,901 B1 | 12/2002 | Royer |
| 6,635,280 B2 | 10/2003 | Shell et al. |
| 6,638,532 B2 | 10/2003 | Rudnic et al. |
| 6,730,320 B2 | 5/2004 | Rudnic et al. |
| 6,958,161 B2 | 10/2005 | Hayes et al. |
| 7,008,631 B2 | 3/2006 | Ashley |
| 7,014,858 B2 | 3/2006 | Ashley |
| 7,201,923 B1 | 4/2007 | van Lengerich |
| 7,211,267 B2 | 5/2007 | Ashley |
| 7,232,572 B2 | 6/2007 | Ashley |
| 7,485,319 B2 | 2/2009 | deVries et al. |
| 7,749,532 B2 | 7/2010 | Chang et al. |
| 7,910,128 B2 | 3/2011 | Chang et al. |
| 7,939,570 B2 | 5/2011 | Raul et al. |
| 7,951,398 B2 | 5/2011 | Dietrich et al. |
| 7,951,403 B2 | 5/2011 | Friesen et al. |
| 7,976,870 B2 | 7/2011 | Berner et al. |
| 7,976,871 B2 | 7/2011 | Vaya et al. |
| 8,052,983 B2 | 11/2011 | Ashley |
| 8,071,075 B2 | 12/2011 | Reed et al. |
| 8,088,726 B2 | 1/2012 | Yamamoto et al. |
| 8,114,062 B2 | 2/2012 | Muni et al. |
| 8,114,385 B2 | 2/2012 | Tamarkin et al. |
| 8,133,510 B2 | 3/2012 | Bartholomaeus et al. |
| 8,137,684 B2 | 3/2012 | Desai et al. |
| 8,192,749 B2 | 6/2012 | Ashley |
| 8,202,912 B2 | 6/2012 | Curatolo et al. |
| 8,206,740 B2 | 6/2012 | Chang et al. |
| 2002/0044968 A1 | 4/2002 | van Lengerich |
| 2003/0077301 A1 | 4/2003 | Maibach et al. |
| 2003/0091630 A1 | 5/2003 | Louie-Helm et al. |
| 2003/0104052 A1 | 6/2003 | Berner et al. |
| 2003/0133985 A1 | 7/2003 | Louie-Helm et al. |
| 2003/0180362 A1 | 9/2003 | Park et al. |
| 2003/0211156 A1 | 11/2003 | Dansereau et al. |
| 2004/0115261 A1 | 6/2004 | Ashley |
| 2004/0147492 A1 | 7/2004 | Ashley |
| 2004/0185097 A1 | 9/2004 | Kannan et al. |
| 2004/0185105 A1 | 9/2004 | Berner et al. |
| 2004/0228915 A1 | 11/2004 | Noack et al. |
| 2005/0037071 A1 | 2/2005 | Cao et al. |
| 2005/0049210 A1 | 3/2005 | Murthy et al. |
| 2005/0152975 A1 | 7/2005 | Nakagami et al. |
| 2005/0266077 A1 | 12/2005 | Royer |

(Continued)

FOREIGN PATENT DOCUMENTS

| | | |
|---|---|---|
| WO | WO 95/31972 A1 | 11/1995 |
| WO | WO 98/09597 A2 | 3/1998 |

(Continued)

OTHER PUBLICATIONS

Co-pending U.S. Appl. No. 13/536,052 inventors Bakan, D.A., et al., filed Jun. 28, 2012 (Filed With Request For Non-Publication).

(Continued)

*Primary Examiner* — Snigdha Maewall

(74) *Attorney, Agent, or Firm* — John E. Thomas, Esq.; Harter Secrest & Emery LLP

(57) ABSTRACT

The present disclosure relates to dosage forms, e.g., swell, float and bioadhesive, and methods that enhance the absorption of doxycycline in the gastrointestinal tract. The oral dosage forms control the spatial and temporal delivery of doxycycline in the gastrointestinal tract. This controlled spatial and temporal delivery provides a site and rate of release, respectively, of the doxycycline into the gastrointestinal tract that enhances the amount of the doxycycline absorbed into the bloodstream.

11 Claims, No Drawings

(56) References Cited

U.S. PATENT DOCUMENTS

| | | |
|---|---|---|
| 2006/0018933 A1 | 1/2006 | Vaya et al. |
| 2006/0057073 A1 | 3/2006 | Lintz et al. |
| 2007/0141096 A1 | 6/2007 | Van Lengerich |
| 2007/0148235 A1 | 6/2007 | Nakagami et al. |
| 2008/0014257 A1 | 1/2008 | He et al. |
| 2008/0070873 A1 | 3/2008 | Alekshun et al. |
| 2008/0161273 A1 | 7/2008 | Arsonnaud et al. |
| 2008/0200533 A1 | 8/2008 | Krishnan |
| 2008/0233206 A1 | 9/2008 | Chomczynski |
| 2008/0248107 A1 | 10/2008 | Pilgaonkar et al. |
| 2008/0268045 A1* | 10/2008 | Dervieux et al. ............ 424/468 |
| 2008/0312168 A1 | 12/2008 | Pilgaonkar et al. |
| 2008/0312193 A1 | 12/2008 | Assefa et al. |
| 2008/0318910 A1 | 12/2008 | Desjardins et al. |
| 2009/0011006 A1 | 1/2009 | Chang et al. |
| 2009/0053310 A1 | 2/2009 | Pilgaonkar et al. |
| 2009/0110728 A1 | 4/2009 | Rastogi et al. |
| 2009/0136568 A1 | 5/2009 | Lukas |
| 2009/0220611 A1 | 9/2009 | Dargelas et al. |
| 2009/0220613 A1 | 9/2009 | Odidi et al. |
| 2010/0184714 A1 | 7/2010 | Raul et al. |
| 2010/0215744 A1 | 8/2010 | Watt et al. |
| 2010/0291191 A1 | 11/2010 | Shoichet et al. |
| 2010/0291201 A1 | 11/2010 | Shah et al. |
| 2010/0305309 A1 | 12/2010 | Ho et al. |
| 2010/0330180 A1 | 12/2010 | Lukas |
| 2011/0027389 A1 | 2/2011 | Dunn |
| 2011/0052682 A1 | 3/2011 | Fatmi et al. |
| 2011/0104206 A1 | 5/2011 | Nanduri et al. |
| 2011/0117184 A1 | 5/2011 | Bromley et al. |
| 2011/0117197 A1 | 5/2011 | Emanuel et al. |
| 2011/0152212 A1 | 6/2011 | Crowther et al. |
| 2011/0159049 A1 | 6/2011 | Nakagami et al. |
| 2011/0171299 A1 | 7/2011 | deVries et al. |
| 2011/0171308 A1 | 7/2011 | Zhang et al. |
| 2011/0177165 A1 | 7/2011 | Gerber et al. |
| 2011/0212156 A1 | 9/2011 | Chang et al. |
| 2011/0223203 A1 | 9/2011 | Berkland et al. |
| 2011/0229569 A1 | 9/2011 | Pilgaonkar et al. |
| 2011/0244043 A1 | 10/2011 | Xu et al. |
| 2011/0262542 A1 | 10/2011 | Ashley |
| 2011/0264028 A1 | 10/2011 | Ramdas et al. |
| 2011/0268666 A1 | 11/2011 | Friedman et al. |
| 2011/0268807 A1 | 11/2011 | Su et al. |
| 2011/0287094 A1 | 11/2011 | Penhasi et al. |
| 2011/0288056 A1 | 11/2011 | Chang et al. |
| 2011/0294902 A1 | 12/2011 | Curatolo et al. |
| 2011/0301129 A1 | 12/2011 | Berner et al. |
| 2011/0305643 A1 | 12/2011 | Gurge et al. |
| 2011/0319368 A1 | 12/2011 | Chang et al. |
| 2012/0009290 A1 | 1/2012 | Segond et al. |
| 2012/0021009 A1* | 1/2012 | Prinderre et al. ............ 424/400 |
| 2012/0028929 A1 | 2/2012 | Power et al. |
| 2012/0035121 A1 | 2/2012 | Rudnic et al. |
| 2012/0039969 A1 | 2/2012 | Bar-Shalom et al. |
| 2012/0045486 A1 | 2/2012 | Bravo Cordero et al. |
| 2012/0045504 A1 | 2/2012 | Whitehead et al. |
| 2012/0076766 A1 | 3/2012 | Phillips et al. |
| 2012/0108552 A1 | 5/2012 | Ashley |

FOREIGN PATENT DOCUMENTS

| | | |
|---|---|---|
| WO | WO 98/56360 A2 | 12/1998 |
| WO | WO 00/21504 A1 | 4/2000 |
| WO | WO 02/47607 A2 | 6/2002 |
| WO | WO 02/083106 A1 | 10/2002 |
| WO | WO 03/035029 A1 | 5/2003 |
| WO | WO 03/035041 A1 | 5/2003 |
| WO | WO 03/063834 A1 | 8/2003 |
| WO | WO 03/075852 A2 | 9/2003 |
| WO | WO 03/086344 A1 | 10/2003 |
| WO | WO 03/086366 A1 | 10/2003 |
| WO | WO 2004/000276 A1 | 12/2003 |
| WO | WO 2004/000360 A1 | 12/2003 |
| WO | WO 2004/041253 A1 | 5/2004 |
| WO | WO 2004/062577 A2 | 7/2004 |
| WO | WO 2004/066910 A2 | 8/2004 |
| WO | WO 2004/087175 A1 | 10/2004 |
| WO | WO 2004/091483 A2 | 10/2004 |
| WO | WO 2004/112713 A2 | 12/2004 |
| WO | WO 2005/011707 A1 | 2/2005 |
| WO | WO 2005/016311 A1 | 2/2005 |
| WO | WO 2005/025488 A2 | 3/2005 |
| WO | WO 2005/046651 A1 | 5/2005 |
| WO | WO 2007/004236 A2 | 1/2007 |
| WO | WO 2007/036671 A2 | 4/2007 |
| WO | WO 2007/036952 A2 | 4/2007 |
| WO | WO 2007/038867 A1 | 4/2007 |
| WO | WO 2007/052289 A2 | 5/2007 |
| WO | WO 2007/087416 A2 | 8/2007 |
| WO | WO 2007/112581 A1 | 10/2007 |
| WO | WO 2008/001341 A1 | 1/2008 |
| WO | WO 2008/104996 A2 | 9/2008 |
| WO | WO 2009/150514 A1 | 12/2009 |
| WO | WO 2010/033800 A2 | 3/2010 |
| WO | WO 2010/035273 A2 | 4/2010 |
| WO | WO 2010/038237 A2 | 4/2010 |
| WO | WO 2010/075065 A2 | 7/2010 |
| WO | WO 2010/132819 A1 | 11/2010 |
| WO | WO 2010/138837 A2 | 12/2010 |
| WO | WO 2011/044208 A1 | 4/2011 |

OTHER PUBLICATIONS

Co-pending U.S. Appl. No. 13/890,173 inventors Chandran, S., et al., filed May 8, 2013 (Not Yet Published).

\* cited by examiner

GASTRORETENTIVE DOSAGE FORMS FOR DOXYCYCLINE

RELATED APPLICATIONS

This application claims the benefit of U.S. Provisional Application No. 61/501,888, filed on Jun. 28, 2011; U.S. Provisional Application No. 61/508,459, filed on Jul. 15, 2011; U.S. Provisional Application No. 61/508,468, filed on Jul. 15, 2011; U.S. Provisional Application No. 61/508,484, filed on Jul. 15, 2011; U.S. Provisional Application No. 61/508,158, filed on Jul. 15, 2011; and U.S. Provisional Application No. 61/508,338, filed on Jul. 15, 2011; all of which are incorporated herein by reference in their entireties.

BACKGROUND

Doxycycline, when administered in currently available dosage forms has various side effects. These side effects include loss of appetite; diarrhea; esophageal issues including dysphagia, esophagitis, and esophageal ulcerations; glossitis, oral inflammation; nausea, and vomiting. It would therefore be desirable to develop a dosage form that regulates the delivery and/or absorption of doxycycline so that the incidence of side effects in human patients is reduced or eliminated without compromising therapeutic efficacy.

SUMMARY

The present disclosure relates to compositions and methods for enhancing the absorption of doxycycline in the gastrointestinal tract along with methods for treating one or more diseases with the composition described herein. More particularly, the present disclosure relates to oral dosage forms of doxycycline, e.g., floating, swelling, and bioadhesive dosage forms, that control the spatial and temporal delivery of doxycycline in the gastrointestinal tract. This controlled spatial and temporal delivery provides a site and rate of release of the doxycycline into the gastrointestinal tract that enhances the amount of the doxycycline absorbed into the bloodstream, thereby enhancing bioavailability of the doxycycline and concomitantly reducing the quantity of doxycycline required to be administered to a patient.

In certain embodiments, the present disclosure provides dosage forms and methods of administration that enhances the absorption of doxycycline in the gastrointestinal tract.

In other embodiments, the present disclosure further provides dosage forms and methods of administration that enhance bioavailability of the doxycycline.

In other embodiments, the present disclosure provides a spatial and temporal delivery of doxycycline in the gastrointestinal tract resulting in improved bioavailability and absorption of the doxycycline into the bloodstream. In some embodiments, the improved bioavailability after a single dose administration is at least about 50% relative to the bioavailability of immediate release formulations.

In some embodiments, the present disclosure provides improved bioavailability of doxycycline, yet side effects, particularly gastrointestinal side effects, are reduced or minimized. In particular, the improved bioavailability can be achieved while maintaining therapeutic efficacy with an otherwise reduced amount of doxycycline administered to the patient, and yet still minimizes or reduce side effects, particularly gastrointestinal side effects.

In still further embodiments, the present disclosure provides that the improved bioavailability is achieved with an otherwise reduced amount of the doxycycline administered to the person or patient.

In another embodiment, the present disclosure provides that the spatial delivery of the doxycycline is targeted to one or more specific areas of the gastrointestinal tract, namely the stomach or the duodenum portion of the small intestine or a combination thereof.

In a further embodiment, the present disclosure provides that the temporal delivery of the doxycycline controls the rate and manner of release of the doxycycline into the desired, specific area. Significantly, the temporal delivery can be metered. It can also be precisely targeted to commence release at a specific period of time after administration and sustain release for as long as possible in the desired, specific area. For example, when the desired spatial area is the stomach and duodenum, the temporal delivery should commence preferably within from about 2.5 to about 5 hours after administration to the patient. In these embodiments, the release in the duodenum should occur within about 2 hours after arrival in the duodenum. If the spatial area is only the stomach, the release of the doxycycline should occur within about 2.5 hours after administration. If the spatial area is only the duodenum, the release occurs within about 2 hours after arrival in the duodenum.

In certain embodiments, about 60 wt % to about 80 wt % of the doxycycline is released in the stomach and about 40 wt % to about 20 wt % of the doxycycline is released in the duodenum. In yet other embodiments, about 20 wt % to about 40 wt % of the doxycycline is released in the stomach and about 80 wt % to about 40 wt % of the doxycycline is released in the duodenum of the patient. In some embodiments, the doxycycline release in the stomach and duodenum takes place at ratios of about 70% stomach to about 30% duodenum, or about 30% stomach to about 70% duodenum, by weight. In other embodiments, the release ratios between the stomach and duodenum can be adjusted slightly to maximize bioavailability, minimize adverse events, reduce the administered dose, and address any reflux react that normally accompanies ingestion of doxycycline.

In certain embodiments, the dosage form provides a tmax and Cmax of doxycycline at appropriate levels such that gastrointestinal side effects are substantially diminished or eliminated.

In certain embodiments, the AUC obtained with a dosage form described herein can have a relatively flat increase.

In certain embodiments, the doxycycline can be in its monohydrate form.

In other embodiments, the doxycycline oral dosage forms may be floatable or swellable or bioadhesive or osmotic or any combination thereof and have an immediate or delayed or extended or pulsatile release or any combinations of such releases.

DETAILED DESCRIPTION

As stated above, the present disclosure provides dosage forms and methods of administration that enhances the absorption of doxycycline in the gastrointestinal tract. The enhanced absorption achieves enhanced bioavailability of the doxycycline in the person or patient. The dosage forms and methods of the present disclosure, provide for a focused spatial and temporal delivery of doxycycline in the gastrointestinal tract, which improves bioavailability and absorption of the doxycycline into the bloodstream.

In all embodiments of the present disclosure, the tmax and the maximum plasma concentration (Cmax) of doxycycline that is present in the dosage forms are at appropriate levels so that gastrointestinal side effects are substantially diminished or eliminated. It is believed that a more constant pharmacokinetic (PK) profile providing a stable plasma concentration of doxycycline over a sustained period of time will result in an improved drug exposure profile (as measured by the area under the concentration vs. time curve (AUC) profile) that will allow lower overall dosing so that side effects are reduced or minimized without compromising therapeutic efficacy. When stating that side effects are minimized, it is meant that the number of (incidence) and/or the severity of the incidences are minimized. Minimization should result in the dosage form having little or substantially no side effects or a diminution and possible elimination of side effects as compared to known doxycycline dosage forms for treating acne.

The present disclosure further provides that tmax and Cmax are established at appropriate levels such that there is a maximization of bioavailability concurrent with a reduction or minimization of side effects. The doxycycline plasma concentration vs. time profile can be a relatively flat profile and thereby provide a substantially constant AUC value.

The present disclosure has improved bioavailability that is defined as a bioavailability that is at least about 50% bioavailability relative to an immediate release dosage forms, yet maintains or reduces side effects, particularly gastrointestinal side effects. The improved bioavailability can be at least about 50%, at least about 70%, at least about 85% to about 90% greater, or at least about 90%, relative to the bioavailability of an immediate release dosage form. In certain embodiments, the bioavailability of the doxycycline in the dosage form described herein can be an absolute bioavailability of at least about 50%, at least about 70%, at least about 85% to about 90%, or at least about 90% of the doxycycline therein.

Again, the improved bioavailability is achieved with a reduction of the amount of doxycycline that would otherwise be needed to be delivered to the person or patient to achieve a given therapeutic effect. It is believed that physical retention and controlled temporal release of the doxycycline from an oral dosage form in desired spatial areas, such as the stomach or the duodenal portion of the small intestine, or a combination of both, will provide the enhanced bioavailability. Relative bioavailability is determined via methods known in the art using conventional measures such as AUC and dose.

It should be noted that the duodenal portion of the small intestine, and not the entire small intestine, is the area of retention outside of the stomach that is desired because doxycycline is in its most lipophilic form and is most stable at the pH found in the duodenum. Lipophilicity promotes absorption across the gut wall. Achieving the desired residency time the duodenum, however, is difficult. Therefore, some embodiments use delivery and absorption in the stomach since absorption in the stomach can be achieved for a much longer duration than in the duodenum.

Significantly, the temporal delivery of the doxycycline controls the rate, duration, and manner of release of the doxycycline into the desired, specific area. Preferably, the temporal delivery can be metered. Also, it can be precisely targeted to commence release at a specific period of time after administration and maintain release for as long as possible in the desired, specific area. The release profile of the present disclosure can have a metered, steady release as part of its modified release profile. As used herein, metered, steady release profile means a release profile that controls the amount released at any given time over a given period of time. In certain embodiments, the metered, steady release can be a constant release.

In some embodiments, doxycycline is released in both the stomach and the small intestine. The doxycycline release in the stomach can be an immediate release, an extended release, a pulsatile release, or a combination of any of the foregoing. The release of doxycycline in the small intestine can be an extended release, a delayed release, a pulsatile release of doxycycline, or a combination of any of the foregoing.

The dosage form of the doxycycline controls the rate of release of the doxycycline into the desired, specific area. Significantly, the temporal delivery can be metered, slow and continuous. It can also be precisely targeted to commence release at a specific period of time after administration and sustain release for as long as possible in the desired, specific area for as long as possible. For example, when the desired area is the stomach and the small intestine, the delivery can be completed within from about 2.5 to about 7 hours after administration to the patient. In these embodiments, the release in the stomach can be completed within about 2.5 to about 5 hours after administration and subsequent release in the small intestine can occur within about 2 hours after arrival in the small intestine. If the release area is only the stomach, the release of the doxycycline can be completed within about 2.5 to about 5 hours after administration. If the release area is only the small intestine, the release can occur within about 2 hours after arrival in the small intestine. Where the release is desired either entirely in the stomach or the duodenum, greater than about 90 wt % of the doxycycline can be released in the desired area.

In some embodiments in which the doxycycline is released in both the stomach and the duodenum, the amount released in each area is controlled. For example, in some embodiments, about 60 wt % to about 80 wt % of the doxycycline can be released in the stomach and about 40 wt % to about 20 wt % of the doxycycline can be released in the duodenum. In yet other embodiments, about 20 wt % to about 40 wt % of the doxycycline can be released in the stomach and about 80 wt % to about 60 wt % of the doxycycline can be released in the duodenum of the patient. In some embodiments, the doxycycline release in the stomach and duodenum takes place at a ratio of about 70% stomach to about 30% duodenum; or about 30% stomach to about 70% duodenum, by weight. In other embodiments, the release ratios between the stomach and duodenum can be adjusted slightly to maximize bioavailability, minimize adverse events, reduce the administered dose, and address any reflux that normally accompanies ingestion of doxycycline.

In embodiments in which there is targeted release in the small intestine, whether in part or entirely, the release or delivery of at least 90 wt % of available doxycycline can occur within 2 hours upon arrival in the duodenum.

The floatable, swellable, and bioadhesive dosage forms of doxycycline can be formulated to have extended-release profiles of desired duration. For instance, in certain embodiments, a 2.5-hour release profile in simulated gastric fluid (SGF) can have a release of about 35% to about 60% in 1 hour and at least about 90% in 2.5 hours. In other embodiments, a 4-hour release profile in SGF can have a release of about 5% to about 65% at 1 hour and at least 75% at 4 hours. In another embodiment, a 4-hour release profile in SGF can have a release of about 35% to about 50% in 1 hour, about 60% to about 75% in 2 hours, and at least about 90% in 4 hours. In still another embodiment, a 5-hour release profile in SGF can have a release of about 25% to about 40% in 1 hour, about 50% to about 70% in 3 hours, and at least about 90% in 5 hours. Extended release dosage forms can be formulated to release doxycycline in the stomach and/or the small intestine as desired.

The floatable, swellable, and bioadhesive dosage forms can also be formulated to provide delayed-release profiles for doxycycline of a desired duration. For instance, the dosage form can be designed such that delayed release occurs in the small intestine, if desired. When formulated with an enteric coating, a dosage form can have a delayed release of at least about 90 wt % of doxycycline release within about 2 hours to about 5 hours after arrival in the small intestine, e.g., release of at least about 90 wt % of doxycycline within about 2 hours to about 5 hours in simulated intestinal fluid (SIF).

The dosage forms of the present disclosure have a therapeutically effective amount of doxycycline and a controlled dissolution profile as assessed in a simulated gastrointestinal tract. This controlled dissolution profile provides for improved and enhanced doxycycline release properties and subsequent absorption.

The controlled dissolution profiles of the disclosed dosage forms reduce the total amount of the doxycycline needed to effect therapeutic treatment of acne to levels lower than would otherwise be delivered to the patient to achieve the same therapeutic effect. Further, the reduced dosing levels associated with the disclosed dosage forms provide for a lower overall exposure to doxycycline in the patient and a reduction or minimization of side effects.

In an exemplary embodiment of the present disclosure, the dosage form can have a therapeutically effective amount of doxycycline, and a dissolution profile that includes 5%-65% dissolution at 1 hour in a simulated gastrointestinal tract or dissolution apparatus containing simulated gastric fluid and at least 75% dissolution at 4 hours in the simulated gastrointestinal tract or dissolution apparatus containing simulated gastric fluid.

In other exemplary embodiments, the dissolution profile can be 50% or less, about 5% to about 50%, or about 40% or less, all at 1 hour. In certain embodiments, the 1 hour dissolution profile can be maintained while at least about 75% of the doxycycline is dissolved at 4 hours, again as measured in the simulated gastrointestinal tract. In another exemplary embodiment, the dissolution profile can be about 35% to about 60% at 1 hour and at least 90% at 2.5 hours in a simulated gastrointestinal tract. In a further exemplary embodiment, the dissolution profile can be about 35% to about 50% at 1 hour, about 60% to about 75% at 2 hours, and at least 90% at 4 hours in a simulated gastrointestinal tract.

The present disclosure includes dosage forms for the treatment of acne comprising a therapeutic amount of doxycycline, and a carrier system having one of the above dissolution profiles. For example, in one embodiment, the carrier system can have a dissolution profile of 5%-65% dissolution at 1 hour in a simulated gastrointestinal tract and at least 75% at 4 hours in a simulated gastrointestinal tract. Again, further exemplary embodiments, can have the carrier system dissolution profile be about 50% or less, about 5% to about 50%, or about 40% or less, all at 1 hour. In certain embodiments, the 1 hour dissolution profile can be maintained while at least about 75% of the doxycycline is dissolved at 4 hours, again as measured in the simulated gastrointestinal tract. Further, as noted above, the carrier system can have a dissolution profile that is about 35% to about 60% at 1 hour and at least 90% at 2.5 hours in a simulated gastrointestinal tract; or about 35% to about 50% at 1 hour, about 60% to about 75% at 2 hours, and at least 90% at 4 hours in a simulated gastrointestinal tract.

Simulated gastrointestinal tract as used herein means as measured in a device that provides a simulated gastric fluid (SGF) that is 750 ml diluted HCl pH 1.1 using USP dissolution apparatus 2 (paddle) at a speed of 75 RPM and a temperature of 37° C., and/or simulated intestinal fluid (SIF) that is 750 ml diluted HCl pH 1.1+200 ml phosphate buffer pH 6 using USP dissolution apparatus 2 (paddle) at a speed of 75 RPM and a temperature of 37° C. The buffer is 0.1 N NaOH in 200 mM Phosphate Buffer adjusted to pH 6.0 using 2 N HCl and/or 2N NaOH.

As used in the present disclosure, the term "doxycycline" includes doxycycline freebase, pharmaceutically acceptable salts thereof, and derivatives thereof, including but not limited to esters, polysaccharides, and hydrates. Useful forms of doxycycline for the present disclosure include, but are not limited to, doxycycline free base, doxycycline monosodium salt, doxycycline calcium salt, doxycycline phosphate, doxycycline carrageenate, doxycycline monohydrate, doxycycline hyclate, doxycycline succinate, and doxycycline hydrochloride. In certain embodiments, doxycycline monohydrate is preferred.

According to another embodiment of the present disclosure, the doxycycline dosage form for the treatment of acne has a therapeutically effective amount of doxycycline, and a carrier system having a modified release profile that provides an increase in the bioavailability of the doxycycline relative to immediate release dosage forms of doxycycline. The increase in bioavailability allows for up to a 30% reduction in the amount of doxycycline used in a dosage form relative to presently available therapies while retaining therapeutic efficacy in the treatment of acne. In yet another embodiment, the reduction in the amount of doxycycline used in a dosage form while retaining therapeutic efficacy in the treatment of acne is up to 20% relative to presently available therapies.

In an embodiment, the dosage forms contemplated range from about 10 mg to about 200 mg of doxycycline based on doxycycline base equivalent weight. In other embodiments, the dosage form includes from about 60 mg to about 180 mg of doxycycline based on doxycycline base equivalent weight. Particular dosage forms include those of 60 mg, 120 mg, and 180 mg. In another embodiment, the dosage forms contemplated range from about 40 mg to about 180 mg of doxycycline based on doxycycline free base equivalent weight. Particular dosage forms include those of 55 mg, 80 mg, 105 mg and 130 mg. In a further embodiment, the dosage form includes from about 10 mg to about 40, about 35, or about 30 mg doxycycline based on doxycycline base equivalent weight.

It is understood that for the dosage forms described herein, and thus the methods of treatment, that to achieve the desired spatial and temporal effects mentioned above, the physical form of the dosage form and the physical properties thereof can be tailored accordingly. The dosage forms can assume structures or formats that provide a variety of different physicochemical profiles or properties. For example, the dosage forms can be a capsule, a tablet, or a gel cap, and can be floating, swellable, bioadhesive, osmotic, or any combination thereof. The doxycycline release from the dosage form may be osmotically regulated either alone or in combination with one or more of the above noted dosage forms. The structure of the dosage form, the release rate of the doxycycline, the physical construction of the dosage forms, and the ingredients thereof and therein will result in the dosage form reaching the target area(s) and having the desired temporal and spatial properties.

A variety of suitable dosage forms for use in this disclosure are well-known in the art, and can be prepare using conventional components. The following description of certain preferred dosage forms is intended to be illustrative of the invention. The dosage forms of this disclosure include dosage forms that combine certain desirable properties, such as any combination of floatable, swellable, bioadhesive, and osmotic.

Floatable Dosage Forms

A floating dosage form is a dosage form that substantially floats at the top surface or in proximity to the top surface of the gastric fluid in the stomach or upper gastrointestinal tract. Floating allows the dosage form to stay in the stomach or upper gastrointestinal tract longer than without floating. Floatable dosage forms typically contain a water-swellable polymer or gel-forming hydrocolloid therein that expands upon contact with the aqueous gastric fluid, thereby reducing the density of the dosage form and creating a buoyancy effect. Gas entrapped in pockets within the matrix of the swelled polymer or gel-forming hydrocolloid can also provides a buoyancy effect. Organic or inorganic excipients can also be included in the floatable dosage form. For example, certain excipients can reduce the density of the dosage form leading to floatability.

According to an embodiment of the present disclosure, the floating dosage form has an amount of doxycycline, an amount of a water-swellable polymer or a gel-forming hydrocolloid, and an amount of an effervescent or gas-generating agent that can generate carbon dioxide (or other gas) upon contact with an acidic aqueous medium. The water-swellable polymer or gel-forming hydrocolloid is capable of retaining at least a portion of the gas generated upon contact with the acidic aqueous medium and thereby controls the spatial localization of the dosage form by causing it to float on or near the surface of the acidic gastric medium. This localization facilitates the subsequent delivery of the doxycycline into the stomach and/or small intestine. The water-swellable polymer or gel-forming hydrocolloid can further control the temporal release of the doxycycline from the dosage form.

The floating dosage form can be a non-biphasic extended release form using a floating mechanism other than organic excipients, such as gas-generating agents or microporous beads.

In accordance with the present disclosure, there is provided a method of treating acne in a human patient by administering any one of the floatable oral dosage forms to the patient once per day.

In particular embodiments, the dosage for is both floatable and bioadhesive, as described herein. In other embodiments, the dosage form is floatable, swellable, and bioadhesive.

The floatable dosage form can also be used in conjunction with an osmotic dosage release. As described elsewhere herein, the osmotic controlled or regulated release dosage form uses salt content in its interior to create an osmotic gradient with respect to the gastric juice or intestinal fluid to induce or drive liquid infiltration therein that results in the release of the doxycycline at a constant rate.

Swellable Dosage Forms

A swellable dosage form is a dosage form that swells upon contact with gastric juice and expands to assume a volume larger than the original volume. Swelling makes the dosage form too large to readily pass through the pyloric sphincter between the stomach and duodenum and allows the dosage form to stay in the stomach longer than without swelling. Swelling typically occurs when a water-swellable polymer within the dosage form expands upon contact with the aqueous gastric fluid. In a particular embodiment, a swellable dosage form may swell to several times its original (non-swelled) volume. A preferred dosage form will retain mechanical rigidity after swelling sufficient to enable it to withstand peristalsis and mechanical contraction of the stomach.

According to an embodiment of the present disclosure, the swellable dosage form can be an oral dosage form in the form of a tablet that has a first layer and a second layer. The first layer includes an amount of one or more polymers or other excipients that are water-swellable and bioadhesive. The second layer includes an amount of doxycycline and an amount of one or more polymers or other excipients that controls the spatial delivery and/or temporal release of the doxycycline in an aqueous media in the stomach and/or small intestine.

In another embodiment, the swellable dosage form can be an oral dosage form that has an amount of doxycycline and an amount of one or more water-swellable polymers or other excipients. The one or more water-swellable polymers controls the spatial delivery and/or temporal release of the doxycycline in an aqueous media in a targeted area of gastrointestinal tract of a patient, particularly the stomach and/or small intestine.

In yet another embodiment, the swellable dosage form can be an oral dosage form that has a therapeutic amount of doxycycline and a swellable carrier system that renders the dosage form swellable upon contact with gastric fluid. In another embodiment, the dosage form is swellable for at least about three hours.

The swellable dosage form can be an extended release dosage form exhibiting a wide range of rates and extents of expansion or swelling. A swellable dosage form can swell to several times or more of its original (non-swelled) volume, e.g., up to about 2 times, about 4 times, about 8 times, and about 12 times. The swellable extended release dosage form can be in unitary phase. The swellable extended release dosage form can be with monophasic release.

In accordance with an embodiment of the present disclosure, there is provided a method of treating acne in a human patient by administering any one of the swellable oral dosage forms to the patient once per day.

In certain embodiments, the swellable dosage form can also be floatable or buoyant. In certain embodiments, the swellable dosage form can also be bioadhesive. In further embodiments, the swellable dosage form can be bioadhesive and flotable. In other embodiments, the swellable dosage form can also be osmotic.

Bioadhesive Dosage Forms

A bioadhesive dosage form is a dosage form that can adhere to the inner or epithelial wall of the stomach or the small intestine, particularly that of the stomach due to the high incidence of mucus there. Mucus is a hydrated, viscous anionic hydrogel layer protecting the gastric mucosa. Mucus has therein mucin, which is composed of flexible cross-linked glycoprotein polymers. The dosage form can contain one or more bioadhesive polymers that have chains that can intertwine with the chains of the glycoprotein polymers of the mucin. The intertwining of chains creates an adhesion effect. Adhesion increases the retention or residence time of the dosage form in the stomach or small intestine. The retention or residence time of the dosage form is, however, inherently limited by the continuous biological turnover of gastric mucus, which diminishes adhesion of the dosage form to the inner or epithelial wall of the stomach over time.

The dosage form can contain one or more polymers that contain mucus or site-specific ligands that have affinity for, e.g., mucus or the inner epithelial wall of the stomach or small intestine. The ligands can be covalently bonded to a polymer, and suitable ligands include, for example, tetrafunctional anions, such as sodium tetraborate, salts of divalent cations, such as calcium or magnesium chloride, and polycationic agents, such as polylysine, polyarginine, or polymyxin B, and pharmaceutically acceptable salts thereof.

According to an embodiment of the present disclosure, the bioadhesive oral dosage form has an amount of doxycycline and an amount of a bioadhesive polymer that enables the dosage form to adhere to the inner or epithelial wall of the gastrointestinal tract. The bioadhesive polymer controls the spatial delivery and/or temporal release or delivery of the doxycycline in an aqueous media in a targeted area of gastrointestinal tract of a patient, most particularly the stomach and/or small intestine. The dosage form optionally further includes a release controlling polymer which may also assist in controlling the spatial delivery and/or temporal release of the doxycycline, and a binder.

In another embodiment, the bioadhesive oral dosage form has an amount of doxycycline and an amount of one or more bioadhesive polymers. The one or more bioadhesive polymers enable the dosage form to adhere to the inner or epithelial wall of the stomach and/or the small intestine. The one or more bioadhesive polymers controls the spatial delivery and/ or temporal release of the doxycycline in an aqueous media in a targeted area of gastrointestinal tract of a patient, most particularly the stomach and/or the small intestine.

In accordance with the present disclosure, there is provided a method of treating acne in a human by administering any one of the bioadhesive oral dosage forms to the patient once per day.

In certain embodiments, the bioadhesive dosage form can also be floatable or buoyant. In other embodiments, the bioadhesive dosage form can also be a swellable dosage form. In further embodiments, the bioadhesive dosage form can be combined with an osmotic dosage form.

Osmotic Dosage Forms

An osmotic dosage form is a dosage form that uses salt content in its interior to create an osmotic gradient with respect to the gastric juice or intestinal fluid to induce or drive liquid infiltration therein at a rate higher than the rate without the osmotic gradient. The osmotic gradient is counteracted by infiltration-regulating polymers, e.g., HPMC or carbomer, within the dosage form. The salt used to establish the osmotic gradient can be, for example, a pharmaceutically acceptable salt of doxycycline, such as, but not limited to, doxycycline hydrochloride or doxycycline hyclate. Sodium chloride or another inactive pharmaceutically acceptable salt can also be used to establish the gradient.

Again, it is possible for the oral dosage form to exhibit two or more of the physical properties described for the aforementioned dosage form types. For instance, a dosage form can be bioadhesive and swellable or bioadhesive and floatable. For instance, a dosage form can be floatable and swellable. For instance, the dosage form can be swellable and osmotic or floatable and osmotic.

In certain embodiments, additional extended release, and possibly delayed release or pulsatile release dosage forms can be used that do not necessarily exhibit the above-described physical properties to a significant degree. In other words, they release doxycycline in designed profiles without floating or undergoing significant swelling or exhibiting adhesion to the inner stomach or duodenal wall. However, such dosage forms are less preferred.

Release Profiles

Generally, the dosage form can have an immediate, delayed, extended, sustained, pulsatile or any combination of these release profiles. In some embodiments, there is an immediate release but it is in combination with one or more of the other releases.

The present disclosure provides for a modified release or modified release profile that is believed to be more therapeutically effective per amount of doxycycline administered to a patient. The preferred modified release profile has an immediate release component and a delayed release component. The modified release profile regulates the commencement time and duration of the release of the doxycycline into the gastrointestinal tract. The modified release profile also regulates the site of release of doxycycline into the gastrointestinal tract.

The modified release profile is a release selected from the group consisting of delayed; combined immediate and delayed; combined immediate, delayed and prolonged. The modified release profile further is optionally inclusive of a pulsatile release component. The modified release profile is further optionally inclusive an osmotically controlled release component.

Some Release Profiles are Described Below.

(A) "Delayed Release" (DR) means release of the doxycycline is delayed until some time after initial administration. An example of delayed release is passing through the stomach and releasing in the duodenum. For example, a delayed release formulation can start to release doxycycline into the gastrointestinal tract of the user after at least about 3 hours, or after at least about 2.75 hours, or after at least about 2.5 hours, or after at least about 2.25 hours, or after at least about 2 hours, or after at least about 1.75 hours, or after at least about 1.5 hour, or after at least about 1.25 hours, or after at least about, or after at least about 0.75 hour, or after at least about 0.5 hour, or after at least about 0.4 hour, or after at least about 0.3 hour, or after at least about 0.2 hour, or after at least about 0.1 hours following ingestion.

(B) "Extended Release" (ER) means the doxycycline is released in a slow, continuous manner over an extended period of time upon administration of the dosage form to the patient. The extended release can commence immediately or some time later. Expressions such as "prolonged-action," and "sustained-release" have also been used to describe such dosage forms. For example, extended release formulation can release doxycycline into the gastrointestinal tract of the of the user for a period of at least about 48 hours, or at least about 36 hours, or at least about 24 hours, or at least about 18 hours, or at least about 12 hours, or at least about 10 hours, or at least about 8 hours, or at least about 6 hours, or at least about 5 hours, or at least about 4 hours, or at least about 3 hours, or after at least about 2.5 hours, or after at least about 2 hours, or at least about 1.5 hour from ingestion.

(C) "Immediate Release" (IR) means release of doxycycline takes place immediately upon administration of the dosage form to the patient or within a relatively brief period of time thereafter. For example, an immediate release formulation can release at least 80%, or at least 85%, or at least 90%, or at least 95%, or at least 99% of doxycycline into the gastrointestinal tract of the user within a period of less than about 2 hours, or less than about 1.75 hour, or less than about 1.5 hour, or less than about 1.25 hour, or less than about 1 hour, or less than about 0.75 hour, or less than about 0.5 hour, or less than about 0.4 hour, or less than about 0.3 hour, or less than about 0.2 hour, or less than about 0.1 hour from ingestion.

(D) "Pulsatile Release" (PR) means release takes place in a pulse or burst profile and can take place initially upon administration of the dosage form to the patient and/or later or repeatedly after administration. For example, a pulsatile release formulation can release a burst of doxycycline into the gastrointestinal tract of the user about every 0.1 hour, or about every 0.2 hour, or about every 0.3 hour, or about every 0.4 hour, or about every 0.5 hour, or about every 0.6 hour, or about every 0.7 hour, or about every 0.8 hour, or about every 0.9 hour, or about every 1 hour, or about every 1.25 hour, or about every 1.5 hour, or about every 1.75 hour, or about every 2 hours, or about every 2.5 hours, or about every 3 hours, or about every 3.5 hours, or about every 4 hours, or about every 4.5 hours, or about every 5 hours, or about every 5.5 hours, or about every 6 hours, or about every 6.5 hours, or about every 7 hours, or about every 7.5 hours, or about every 8 hours.

(E) "Controlled Release (CR) means any regulation of release of doxycycline and can include immediate release, extended release, delayed release, pulsatile release, and combinations thereof.

(F) "Modified Release" (MR) means the release is any combination of the releases (A) to (E) defined above, except it is not a completely or solely immediate release.

In the embodiments where both the stomach and duodenum are desired to have release of the active therein, the oral dosage forms can have a number of physical characteristics. The dosage form can take the form of any known in the art, such as a tablet, a capsule, a caplet, a gel cap, and a microparticulate. Capsules can be formed of any natural or synthetic water-soluble polymer, such as HPMC or gelatin.

In some embodiments, a dosage form may be coated with an enteric coating material(s) or have such a coating over a component within the dosage form. An enteric coating material can include a coating polymer(s) (or non-polymer(s)) and/or other excipients that is substantially insoluble in the acidic environment of the stomach but is substantially soluble in duodenal/intestinal fluids at certain pH levels, typically in a pH range of about 5 to about 7, more particularly a pH of about 5.5 to about 6.5. The enteric coating material may include a non-toxic, pharmaceutically acceptable polymer, for example, cellulose acetate phthalate (CAP), hydroxypropyl methylcellulose phthalate (HPMCP), polyvinyl acetate phthalate (PVAP), hydroxypropyl methylcellulose acetate succinate (HPMCAS), cellulose acetate trimellitate, hydroxypropyl methylcellulose succinate, cellulose acetate succinate, cellulose acetate hexahydrophthalate, cellulose propionate phthalate, polymeric methacrylates, copolymer of methylmethacrylic acid and methyl methacrylate, copolymer of methyl acrylate, methylmethacrylate and methacrylic acid, copolymer of methylvinyl ether and maleic anhydride (Gantrez ES series), ethyl methyacrylate-methylmethacrylate-chlorotrimethylammonium ethyl acrylate copolymer, natural resin such as zein, shellac and copal collophorium, and commercially available enteric dispersion systems (e.g., EUDRAGIT® L30D55, EUDRAGIT® FS30D, EUDRAGIT® L100, KOLLICOAT® EMM30D, ESTACRYL® 30D, Acryl-EZE®, COATERIC®, and AQUATERIC®).

The coating may also include one or more plasticizers, such as acetyltriethyl citrate, triethyl citrate, acetyltributyl citrate, dibutylsebacate, triacetin, polyethylene glycol, and propylene glycol. The coating may also have an anti-tacking agent such as talc. The enteric coating material will typically be applied at about 1 wt % to about 50 wt % and more typically about 4 wt % to about 25 wt % based on the combined weight of the coating and the remainder of the dosage form. Dosage forms may be coated by any method known in the art, including being applied as aqueous-based solutions, organic-based solutions or dispersions, in which polymer-containing droplets are atomized with air and sprayed onto the substrates (pan coating or fluid bed coating) or being applied electrostatically.

The enteric coating material will typically be applied to the surface of the core, such as tablet core or drug layered microparticulates, at about 1 wt % to about 50 wt % and more typically about 4 wt % to about 25 wt % based on the combined weight of the coating and the tablet core. The tablet cores may be coated by any method known in the art, including being applied as aqueous-based solutions or dispersions, or organic-based solutions or dispersions, in which polymer-containing droplets are atomized with air and sprayed onto the substrates (pan coating or fluid bed coating) or being applied electrostatically.

In another embodiment, the oral dosage form is a tablet or capsule that comprises a therapeutically effective amount of doxycycline, and a specialized polymer, such as a polymer of acrylic acid cross-linked with polyalkenyl ethers or divinyl chloride. The specialized polymer is a dual-purpose polymer capable of enhancing bioadhesion and providing a controlled release of the doxycycline to create a more constant ADME/PK profile for the doxycycline.

In a species of this embodiment, the polymer is a polycarbophil cross-linked with polyalkenyl ethers or divinyl glycol. The bioadhesive properties increase residence time in the stomach, and the controlled release properties can increase the maximum plasma concentration (CMAX) and maintain a long sustained area under the curve (AUC). The bioadhesive and controlled release properties assist with targeted delivery of the doxycycline to the duodenum for possible maximum absorption.

Polymers of acrylic acid useful in this dosage form include a mix of suitable bioadhesive carbomers or polycarbophils, more preferably a polycarbophil; which is a polyacrylic cross-linked with polyalkenyl ethers or divinyl-glycol, and most preferably where the polycarbophil is the Noveon® AA-1 polycarbophil. Noveon® polycarbophils, are polymers of acrylic acid, crosslinked with polyalkenyl ethers or divinyl glycol. These polymers swell in water up to 1,000 times their original volume (and ten times their original diameter) to form gels when neutralized.

Additional polymers useful in this dosage form include multiple polymers (sodium alginates, CMC, polyoxyethylene-polyoxypropylene) and biodegradable polymers such as PLGA and PLA. Examples of biodegradable polymers include (i) polyhydroxy butyrate (PHB); (ii) poly-hydroxybutyrate-co-b-Hydroxy valerate (PHBV; (iii) polyglycolic acid (PGA); (iv) polylactic acid (PLA; and (v) poly(I-caprolactone) (PCL).

In a further embodiment, the dosage forms are a tablet that has a first layer and a second layer. The first layer includes an amount of one or more polymers capable of adhering to at least a portion of the inner wall of the stomach and/or duodenum. The second layer includes an amount of doxycycline and an amount of one or more polymers that controls the delivery of the doxycycline.

The one or more polymers capable of adhering to at least a portion of the inner wall of the stomach and/or duodenum includes a carbomer. The one or more polymers includes hydroxpropylmethylcellulose. Microcrystalline cellulose can be in each of the first and second layers. Also, an amount of mannitol can be in the layer that includes doxycycline.

In another embodiment, the dosage form is preferably a tablet that has an extended-release oral dosage form that has an immediate-release enteric-coated core and an extended-release powder press coating. The core includes a first amount of doxycycline and one or more diluents. The core has an enteric coating thereon. The press coating includes a second amount of doxycycline and an amount of one or more polymers that controls the spatial and temporal delivery of the doxycycline in an aqueous media in a targeted area of gastrointestinal tract of a patient. The one or more diluents in the core include mannitol and sodium starch glycolate. The one or more polymers in the press coating include hydroxypropylmethylcellulose and microcrystalline cellulose.

In still another embodiment, the oral dosage form is preferably a tablet that has an extended-release oral dosage form, having an amount of doxycycline, an amount of carbomer, and an amount of polycarbophil. The dosage form can further include polyvinyl pyrrolidone. The doxycycline in this oral dosage form has a dissolution in aqueous media of about 30% to about 50% in 4 hours, about 60% to about 75% in 8 hours, and at least about 90% in 12 hours. In another embodiment, the doxycycline in this oral dosage form has a dissolution in aqueous media of about 20% to about 40% in 8 hours, about 50% to about 70% in 16 hours, and at least about 80% in 24 hours.

In a further embodiment, the dosage form is preferably a tablet that has an extended-release oral dosage form, having an amount of doxycycline, an amount of carbomer, an amount of polycarbophil, and sodium bicarbonate. The carbomer and the polycarbophil control the spatial and temporal delivery of the doxycycline in an aqueous media in the duodenum, the targeted area of gastrointestinal tract of the patient. In one species of this embodiment, the dosage form is floatable and bioadhesive. The doxycycline has a dissolution in aqueous media of about 35% to about 60% in 1 hour and at least about 90% in 2.5 hours. In another species of this embodiment, the doxycycline has a dissolution in aqueous media of about 25% to about 40% in 1 hour, about 50% to about 70% in 3 hours, and at least about 90% in 5 hours. The release is 2.5 hours and 5 hours in the duodenum.

In another species of this embodiment, this extended release oral dosage form is targeted for the stomach. The dosage form is bioadhesive and floatable, and the release is 2.5 hours and 5 hours in the stomach. The doxycycline in the oral dosage form has a dissolution in aqueous media, in one species of about 35% to about 60% in 1 hour and at least about 90% in 2.5 hours and in another species of about 25% to about 40% in 1 hour, about 50% to about 70% in 3 hours, and at least about 90% in 5 hours.

In a still further embodiment, the dosage form is an extended release tablet having an amount of doxycycline, and an amount of a water-swellable polymer other than pregelatinized starch. The water swellable polymer other than pregelatinized starch controls the spatial and temporal delivery of the doxycycline. The doxycycline has a dissolution in aqueous media of about 35% to about 50% in 1 hour, about 60% to about 75% in 2 hours, and at least about 90% in 4 hours. The dosage tablet can also have an anionic polymer selected from the group consisting of cross-linked acrylic acid polymer, methacrylic acid polymer, alginate, and carboxymethyl cellulose.

In a yet further embodiment, the dosage form is a prolonged release bioadhesive tablet having a polymer of acrylic acid, cross-linked with polyalkenyl ethers or divinyl glycol, and a therapeutically effective amount of doxycycline.

In another embodiment, the oral dosage form is a tablet or capsule that has a pulsatile dosage form having a solid dispersion that includes an amount of doxycycline, one or more organic carriers, one or more diluents, and one or more bioadhesive polymers. In this embodiment, the targeted area can be the duodenum. The one or more organic carriers can be lauric acid, PEG-6000, cetostearyl alcohol, or any combinations thereof. The one or more diluents can be mannitol. The one or more bioadhesive polymers can be hydroxypropylcellulose.

In a further embodiment, the oral dosage form can be a pulsatile oral dosage form in the form of a capsule or tablet that has a solid dispersion that includes an amount of doxycycline, one or more diluents, and one or more bioadhesive polymers. In some embodiments, this oral dosage form can be targeted to the duodenum. The one or more diluents can be mannitol. The one or more bioadhesive polymers can be polycarbophil.

In a still further embodiment, the oral dosage form can be a tablet or a capsule that has a solid dispersion of an amount of doxycycline, an amount of one or more water soluble polymers, and an amount of one or more organic carriers. In some embodiments, this oral dosage form can be targeted to the duodenum. The one or more water soluble polymers can be chitosan. The one or more organic carriers can be glycerol monooleate.

In a yet further embodiment, the oral dosage form can be an extended release tablet or capsule that has an amount of doxycycline, an amount of one or more pH insensitive controlled release polymers, and an amount of one or diluents. In certain embodiments, the dosage form can be targeted to the stomach, duodenum, or a combination thereof.

In another embodiment, the oral dosage form can be an extended release tablet or capsule that has an amount of doxycycline, an amount of one or more controlled release polymers, a buffer, and an amount of one or diluents.

In other embodiments of dosage forms of the present disclosure, the release of doxycycline can be controlled by the use of excipients such as organic carriers and diluents. Useful organic carriers include, but are not limited to, glyceryl monostearate, lauric acid, PEG-6000, and cetostearyl alcohol. Useful diluents include lactose monohydrate and mannitol.

The present disclosure provides a doxycycline dosage form for the treatment of acne that has a minimal, but therapeutically effective amount of doxycycline based on the body weight of the patient, and a carrier system having a modified release profile in which the plasma concentration of doxycycline remains above the minimal therapeutically effective amount of doxycycline for a substantial period of time after the concentration meets or exceeds the minimal therapeutically effective amount of doxycycline and the proportion of the plasma concentration to the minimal therapeutically effective amount of doxycycline remains substantially constant over a substantial period of time.

According to an embodiment of the present disclosure, the doxycycline dosage form for the treatment of acne has a minimal, but therapeutically effective, amount of doxycycline based on the body weight of the patient, and a carrier system having a modified release profile. The modified release profile provides a concentration of doxycycline in the plasma that retains a substantially constant proportion relative to the minimal therapeutically effective amount of doxycycline for a substantial period of time after the concentration meets or exceeds the minimal therapeutically effective amount of doxycycline.

Excipients

In embodiments of dosage forms of the present disclosure, the release of doxycycline can be controlled or regulated by the use of excipients. Excipients can also perform functions other than control or regulation of release of doxycycline. Excipients include, but are not limited to, one or more disintegrants, wetting agents, diluents, carriers or vehicles (solid, semi-solid, or liquid), glidants, colorants, binders, lubricants, release regulating agents, pH adjusting agents, water-swellable polymers, gel-forming hydrocolloids, effervescent or gas generating agents, organic materials, and osmotic agents. A particular excipient may serve multiple functions. Excipients that are generally characterized as falling within one or more of the above categories are well know-in the art, and suitable examples of such excipients are provided herein. The dosage forms described herein can be formulated with any one, or any combination of suitable excipients.

Useful excipients that can control or regulate release of doxycycline from the dosage form of the present disclosure can be polymeric or non-polymeric, organic or inorganic, water-soluble or non-water soluble, or in the form of a solid, semi-solid, or liquid. Useful organic excipients include one or more fatty acids and esters thereof, fatty alcohols, lipid waxes, amphiphilic waxes, and gums. Examples of fatty acids and esters thereof include glyceryl monostearate, glyceryl monooleate, lauric acid, and stearic acid. Examples of fatty alcohols include stearyl alcohol, cetostearyl alcohol, cetyl alcohol, and myristyl alcohol. Examples of gums include acacia, gelatin, tragacanth, veegum, xanthan gum and chitosan. Examples of waxes include beeswax, carnauba wax, spermaceti wax, candelilla wax, cocoa butter, and paraffin. Other useful organic excipients include polymeric glycols, such as polyethylene glycol and propylene glycol. A useful polymeric glycol is PEG-6000.

Useful polymeric excipients include, for example, methyl cellulose (MC), carboxymethylcellulose (CMC), ethylcellulose (EC), hydroxyethyl cellulose (HEC), hydroxypropyl cellulose (HPC), hydroxypropyl methylcellulose (HPMC), hydroxypropyl methylcellulose phthalate, cellulose acetate phthalate, hydroxypropyl methylcellulose succinate, polymers and copolymers of (meth)acrylic acid or (meth)acrylic acid methyl ester, polyvinyl acetate phthalate or polymers or copolymers of polyvinyl acetate, cellulose acetate, cellulose acetate trimellitate, carbomer, polyvinyl pyrrolidone, and any combinations thereof.

Useful disintegrants include, for example, cornstarch, pregelatinized starch, cross-linked carboxymethyl cellulose sodium, sodium starch glycolate, and polyvinylpolypyrrolidone (PVPP). Other useful disintegrants include croscarmellose sodium, crospovidone, starch, alginic acid, sodium alginate, clays (e.g. veegum or xanthan gum), cellulose floc, ion exchange resins, or effervescent systems, such as those utilizing food acids (such as citric acid, tartaric acid, malic acid, fumaric acid, lactic acid, adipic acid, ascorbic acid, aspartic acid, erythorbic acid, glutamic acid, and succinic acid) and an alkaline carbonate component (such as sodium bicarbonate, calcium carbonate, magnesium carbonate, potassium carbonate, ammonium carbonate, etc.).

Examples of useful glidants include silicon dioxide, colloidal silicon dioxide, magnesium trisilicate, powdered cellulose, starch, talc, and tribasic calcium phosphate.

Examples of useful lubricants include stearic acid, magnesium stearate, calcium stearate, talc, and zinc stearate.

Examples of useful wetting agents include sodium lauryl sulfate, poloxamer, and docusate sodium.

Useful diluents or fillers include lactose, lactose, calcium carbonate, dibasic calcium phosphate, tribasic calcium phosphate, calcium sulfate, microcrystalline cellulose, dextran, starch, pregelatinized starch, sucrose, xylitol, lactitol, mannitol, sorbitol, sodium chloride, and polyethylene glycol.

Useful binders include methylcellulose, hydroxyethyl cellulose, hydroxypropyl cellulose, hydroxypropyl methylcellulose, polyvinylpyrrolidone (PVP), and polyvinylpyrrolidone/vinyl acetate copolymer. Other commonly used binders include cellulosic polymers such as carboxymethyl cellulose; microcrystalline cellulose; starch; sugars such as sucrose, glucose, dextrose, lactose; and gums such as guar gum and tragacanth gum.

Swellable polymers useful in the floatable dosage form include, but are not limited to, methylcellulose, ethylcellulose, hydroxypropyl cellulose, carboxymethylcellulose sodium, hydroxypropyl methylcellulose, polycarbonate polymers, polyvinyl acetate, agar, carbomer, polycarbophil, polyethylene oxide, chitosan, and alginate.

Polymers useful in this disclosure for bioadhesive dosage forms, which can bind to any mucosal surface, include water soluble and insoluble, biodegradable and non-biodegradable polymers. The floatable dosage form and swellable dosage form can be used in combination with a bioadhesive polymer. Polymers can include, for example, hydrophilic polymers, hydrogels, and thermoplastic polymers. Examples of polymers include, but are not limited to, carbomer, polycarbophil, polyvinylpyrrolidone, polyvinyl alcohol, polyamides, polycarbonates, polyalkylene glycols, polyvinyl ethers, esters and halides, polyacrylic polymers, polymethacrylic acid, methacrylic acid copolymer (carbomer), polymethylmethacrylic acid, methyl methacrylate, poly(methyl methacrylate), hydroxyethyl methacrylate copolymer, methylcellulose, carboxymethylcellulose, ethylcellulose, hydroxymethylcellulose, hydroxypropyl cellulose, hydroxypropyl methylcellulose, carboxymethylcellulose sodium, ethylene glycol polymers and its copolymers, oxyethylene polymers, polyvinyl acetate, esters of hyaluronic acid, poly(lactides), poly(glycolides), poly(lactide-co-glycolides), polycaprolactones, polyalkyl cyanoacrylates, polyorthoesters, polyphosphoesters, polyanhydrides, polyphosphazenes, alginates, and chitosan. Polycarbophil, a polyacrylic acid cross-linked with polyalkenyl ethers or divinyl-glycol, is an illustrative bioadhesive polymer. Illustrative polycarbophils are Noveon® polycarbophils, particularly Noveon®-AA1.

Another bioadhesive mechanism is the use of polymers derivatized with mucus or site-specific ligands that have high affinity to the specific sites, such as the inner or epithelial wall of the stomach or small intestine. If the bioadhesive is used with a swellable polymer, the swellable polymers can be, but are not limited to, carboxymethylcellulose sodium, methylcellulose, hydroxypropyl methylcellulose, ethylcellulose, hydroxypropyl cellulose, polycarbonate polymers, polyvinyl acetate, agar, carbomer, polycarbophil, polyethylene oxide, alginate, and chitosan.

Suitable gas-generating agents can be any compound or compounds that produce effervescence, such as a solid acid compound and a solid basic compound that, in the presence of a fluid, can react to form a gas, such as carbon dioxide. Examples of acid compounds include, organic acids such as malic, fumaric, tartaric, itaconic, maleic, citric, adipic, succinic and mesaconic, and inorganic acids such as sulfamic or phosphoric, also acid salts such as monosodium citrate, potassium acid tartrate and potassium bitartrate. Examples of basic compounds include, for example, metal carbonates and bicarbonates salts, such as alkali metal carbonates and bicarbonates.

The amount of excipient(s), including bioadhesive and swellable polymers, employed in the dosage form can vary and depend on a number of factors, such as properties of the excipient(s), properties of the doxycycline active, desired doxycycline release profiles, configuration of the dosage form, the process for making the dosage form, the modality of the dosage form, and the mode of administration of the dosage form.

In still other embodiments of dosage forms of the present disclosure, the release of doxycycline can be controlled in both the stomach and duodenum by the use of pH-insensitive controlled-release polymers. In yet other embodiments in which pH-sensitive controlled release polymers are used, buffers may be employed to mediate pH effects on release rates.

To prolong gastric residence time, gas generating excipients, such as carbomer, cellulosic polymers, and chitosan, may be employed.

The dosage form of the present disclosure is preferably configured such that when properly administered, the patient has minimized side effects compared to a placebo. More particularly, the dosage form is preferably configured such that, when administered, there are minimized gastrointestinal side effects, including, but are not limited to: loss of appetite; diarrhea; esophageal issues including dysphagia, esophagitis, esophageal ulcerations; glossitis; oral inflammation; nausea; and vomiting. Other adverse side effects can also be encountered by the use of doxycycline. The dosage form of the present disclosure is effective in minimizing one or more of these side effects. When stating that side effects are minimized, it is meant that the number (incidence) and/or the severity of the incidences are minimized. Minimized should result in the dosage form having little or substantially no side effects or a diminution and possible elimination of side effects.

The dosage form preferably exhibits high levels of bioavailability in human patients yet minimizes side effects sometimes encountered with use of doxycycline that are gastrointestinal side effects that include, but are not limited to: loss of appetite; diarrhea; esophageal issues including dysphagia, esophagitis, esophageal ulcerations; glossitis; oral inflammation; nausea; and vomiting. Other adverse side effects can also be encountered by the use of doxycycline. The dosage form of the present disclosure is effective in minimizing one or more of these side effects.

In one embodiment of the present disclosure, there is provided a method of assisting a physician in prescribing a dose of doxycycline for the treatment of acne. The method includes determining the body weight of a patient, referring to a chart or reference tool that correlates a plurality of body weight ranges with a corresponding number of dosage forms each having a different level of doxycycline based on a target dosage of about 1.2 mg/kg/day, and identifying a single dosage form corresponding to a particular weight range in which the patient's weight falls in the chart or reference tool. The method can include administering to the patient the identified single dosage form.

What is claimed is:

1. A method for increasing the bioavailability of orally administered doxycycline, the method comprising:
controlling the spatial and temporal delivery of the doxycycline administered in an oral dosage form into a gastrointestinal area of a patient in need thereof, wherein the gastrointestinal area is selected from the group consisting of the stomach, duodenum of the small intestine, and a combination thereof;
wherein the oral dosage form has a modified release profile and a swellable physicochemical profile or property and comprises:
a first layer and a second layer, wherein the first layer comprises one or more swellable excipients selected from the group consisting of a cellulose polymer, a polycarbonate polymer, polyvinyl acetate, agar, carbomer, polycarbophil, polyethylene oxide, chitosan, and alginate; and
a second layer comprising doxycycline;
wherein the oral dosage form regulates the site, commencement time, duration and rate of release of doxycycline into the gastrointestinal area of the patient, and the oral dosage form exhibits $t_{max}$ and $C_{max}$ in the patient at sufficient levels so that gastrointestinal side effects are minimized or eliminated;
wherein the controlled temporal release in the gastrointestinal area of the patient is completed in about 2.5 hours to about 7.0 hours after administration to the patient; and
wherein the increased bioavailability is 90% or greater relative to an immediate release doxycycline profile.

2. The method of claim 1, wherein the oral dosage form has a reduction of the amount of doxycycline that would otherwise need to be delivered to the patient to achieve the given therapeutic effect.

3. The method of claim 1, wherein the oral dosage form affects the amount of the doxycycline that is absorbed into the bloodstream when in the gastrointestinal area.

4. The method of claim 1 wherein the release of the doxycycline is substantially entirely in the stomach or substantially entirely in the duodenum.

5. The method of claim 1, wherein the controlled temporal release in the stomach commences at about 2.5 hours after administration to the patient, and the controlled temporal release in the duodenum is within about 2 hours after arrival in the duodenum.

6. The method of claim 1, wherein the doxycycline is selected from the group consisting of doxycycline freebase, doxycycline monohydrate, and doxycycline hyclate.

7. The method of claim 1, wherein the doxycycline release in the stomach and duodenum takes place at ratios of about 70% stomach to about 30% duodenum or about 30% stomach to about 70% duodenum, by weight.

8. The method of claim 1, wherein the modified release profile is selected from the group consisting of delayed, extended, sustained, pulsatile, and any combination thereof.

9. The method of claim 1 wherein the first layer is also bioadhesive and wherein the dosage form is a tablet.

10. The method of claim 1, wherein the oral dosage form is selected from the group consisting of a capsule, tablet, caplet, tablet with a plurality of pellets, capsule with a plurality of pellets, tablet with a specialized polymer, capsule with a specialized polymer, tablet with a pair of layers, tablet with an immediate-release enteric-coated core and an extended-release powder press coating, tablet with a water-swellable polymer other than pregelatinized starch, prolonged release bioadhesive tablet, pulsatile dosage form having a solid dispersion, tablet with a pulsatile dosage form having a solid dispersion, capsule with a pulsatile dosage form having a solid dispersion, tablet with a pH-insensitive controlled release polymer, capsule with a pH-insensitive controlled release polymer, tablet with a pH-sensitive controlled release polymer, capsule with a pH-sensitive controlled release polymer tablet with a controlled release polymer, and capsule with a controlled release polymer.

11. The method of claim 1, wherein the cellulose polymer is selected from the group consisting us methylcellulose, ethylcellulose, hydroxypropyl cellulose, carboxymethylcellulose sodium, hydroxypropyl methylcellulose, and combinations thereof.

* * * * *